US008150709B2

(12) United States Patent
Miller et al.

(10) Patent No.: US 8,150,709 B2
(45) Date of Patent: Apr. 3, 2012

(54) INTEGRATED POINT OF CARE MEDICATION ADMINISTRATION INFORMATION SYSTEM

(75) Inventors: Raymond F. Miller, Lincoln University, PA (US); Alan M. Portnoy, Warwick, PA (US); Deborah A. Saeger, Allentown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 269 days.

(21) Appl. No.: 12/720,705

(22) Filed: Mar. 10, 2010

(65) Prior Publication Data

US 2010/0241456 A1 Sep. 23, 2010

Related U.S. Application Data

(60) Provisional application No. 61/161,818, filed on Mar. 20, 2009.

(51) Int. Cl.
*G06Q 50/00* (2012.01)
(52) U.S. Cl. .................................. 705/2; 705/3
(58) Field of Classification Search ................ 705/2, 3
See application file for complete search history.

(56) References Cited

U.S. PATENT DOCUMENTS

| 7,230,529 | B2 | 6/2007 | Ketcherside, Jr. et al. | |
|---|---|---|---|---|
| 2004/0010425 | A1 | 1/2004 | Wilkes et al. | |
| 2004/0021693 | A1* | 2/2004 | Monteleone | 345/781 |
| 2004/0078231 | A1 | 4/2004 | Wilkes et al. | |
| 2004/0172283 | A1* | 9/2004 | Vanderveen et al. | 705/2 |
| 2004/0199405 | A1 | 10/2004 | Harper et al. | |
| 2004/0204910 | A1* | 10/2004 | Brumbach et al. | 702/185 |
| 2005/0021368 | A1* | 1/2005 | Burkeen et al. | 705/2 |
| 2006/0026205 | A1 | 2/2006 | Butterfield | |
| 2006/0106647 | A1* | 5/2006 | Brummel et al. | 705/3 |
| 2006/0149416 | A1 | 7/2006 | Mohapatra et al. | |
| 2007/0033075 | A1* | 2/2007 | Hoffman et al. | 705/3 |
| 2007/0088458 | A1 | 4/2007 | Laughland et al. | |
| 2007/0168223 | A1 | 7/2007 | Fors et al. | |
| 2008/0065424 | A1 | 3/2008 | Frick | |
| 2008/0082366 | A1 | 4/2008 | Miller et al. | |
| 2008/0097792 | A1 | 4/2008 | Marge | |
| 2009/0164238 | A1* | 6/2009 | Auchinleck | 705/2 |
| 2010/0063847 | A1* | 3/2010 | Eisenberg et al. | 705/3 |

* cited by examiner

*Primary Examiner* — Gerald J. O'Connor
*Assistant Examiner* — Jonathan K Ng
(74) *Attorney, Agent, or Firm* — Alexander J Burke

(57) ABSTRACT

An integrated point of care medication administration system comprises a point of care medication administration system including an interface for communicating with the at least one repository and information sources and including a processor. The processor uses the information and the interface in automatically acquiring for a particular patient, data representing particular patient parameters and laboratory test results associated with a particular individual medication in response to user initiation of an order for the particular individual medication to be administered to the particular patient. A display device presents at least one display image indicating acquired particular patient parameters and laboratory test results of the particular patient and identifying a particular patient parameter or laboratory test result needing to be acquired prior to administration of the particular individual medication to the particular patient.

15 Claims, 3 Drawing Sheets

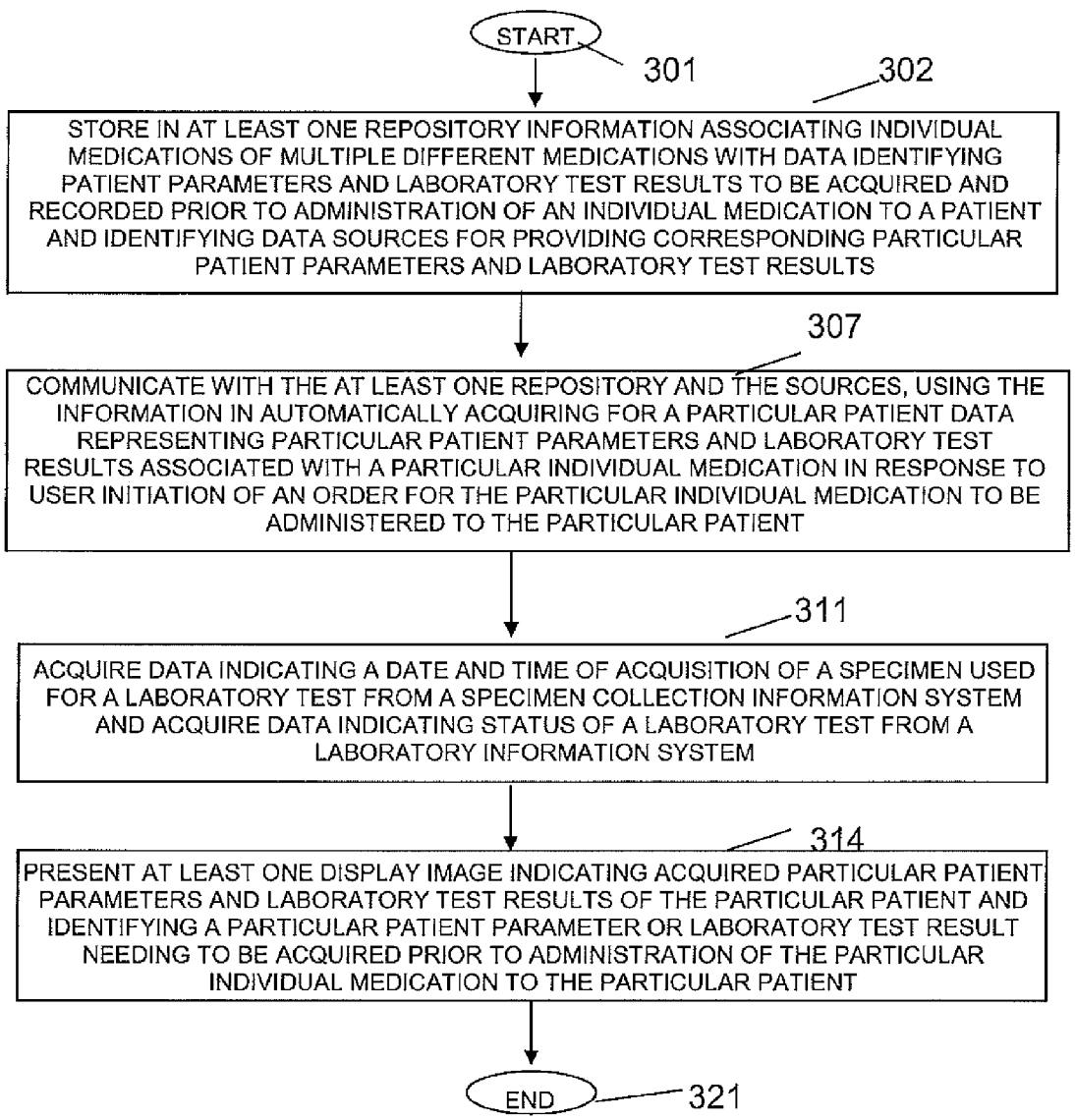

INTEGRATED POINT OF CARE MEDICATION ADMINISTRATION INFORMATION SYSTEM

This is a non-provisional application of provisional application Ser. No. 61/161,818 filed Mar. 20, 2009, by R. F. Miller et al.

FIELD OF THE INVENTION

This invention concerns an integrated point of care medication administration information system for automatically identifying and acquiring data representing particular patient parameters and laboratory test results associated with a particular individual medication for a particular patient in response to user initiation of an order for the particular individual medication to be administered to the particular patient.

BACKGROUND OF THE INVENTION

Clinical data such as vital sign data and laboratory test results need to be reviewed for many medications, prior to administration, to ensure the continued safety and efficacy of each dose. Some of this data needs to be collected at the time of medication administration, while other data is collected and reported at different times (before or after giving the medication). The collection, recording and reporting of this data can be performed by using different methods. However, this information is frequently documented in other ancillary systems or on paper which adds to clinician workload through the need to spend time locating data.

Laboratory test results and vital sign data needs to also be reported and recorded at the appropriate time (e.g. most recent INR (International normalized ratio), aPTT (activated partial thromboplastin time) drawn 4-6 hours prior to a heparin rate change, gentamicin trough level drawn prior to a dose being administered) so that a clinician can make a correct evaluation of patient status. However, it is not always apparent to the clinician that the data that was reported was collected at an incorrect time. Incorrectly reported data can result in an inappropriate clinical decision and patient harm.

In known systems a user manually enters data that is frequently documented in different systems and locations (electronic and manual). There may also be a duplication of work as vital sign data may be collected by a different clinician from the clinician who administers medications. Further, known systems lack data validation making it difficult to identify when a reported vital sign or laboratory test result may not accurately reflect a clinical condition of a patient. A system according to invention principles addresses these deficiencies and related problems.

SUMMARY OF THE INVENTION

A system uses an integrated pharmacy information system and barcode point of care system (BPOC) to identify medications in Pharmacy Drug Master Files that require information to be provided and captured at the time of administration using a BPOC system. An integrated point of care medication administration system includes at least one repository of information. The information associates individual medications of multiple different medications with data identifying patient parameters and laboratory test results to be acquired and recorded prior to administration of an individual medication to a patient and identifying data sources for providing corresponding particular patient parameters and laboratory test results. A point of care medication administration system includes an interface for communicating with the at least one repository and the sources and includes a processor. The processor uses the information and the interface in automatically acquiring for a particular patient, data representing particular patient parameters and laboratory test results associated with a particular individual medication in response to user initiation of an order for the particular individual medication to be administered to the particular patient. A display device presents at least one display image indicating acquired particular patient parameters and laboratory test results of the particular patient and identifying a particular patient parameter or laboratory test result needing to be acquired prior to administration of the particular individual medication to the particular patient.

BRIEF DESCRIPTION OF THE DRAWING

FIG. 3 shows a flowchart of a process used by an integrated point of care medication administration information system, according to invention principles.

DETAILED DESCRIPTION OF THE INVENTION

A system uses an integrated pharmacy information system and point of care system to identify medications in Pharmacy Drug Master Files that require information to be provided and captured at the time of administration using the point of care system. Once a medication is identified, at the time of medication administration, the system automatically acquires the information, presents it to a clinician and stores the information in a database associated with the data indicating the administration of the medication. The system enables a user to configure specific parameters, for each medication, to ensure that information presented to a clinician has been acquired and documented at the appropriate time for a correct clinical assessment to be made. In addition to capturing and recording information at the time of medication administration to provide a clinician with information for making prospective medication management decisions, the system provides additional information that is later utilized to track and identify a trend in responses to medications over time. This allows the clinician to optimize therapeutic outcomes while reducing the risks of adverse events.

Figure 1:
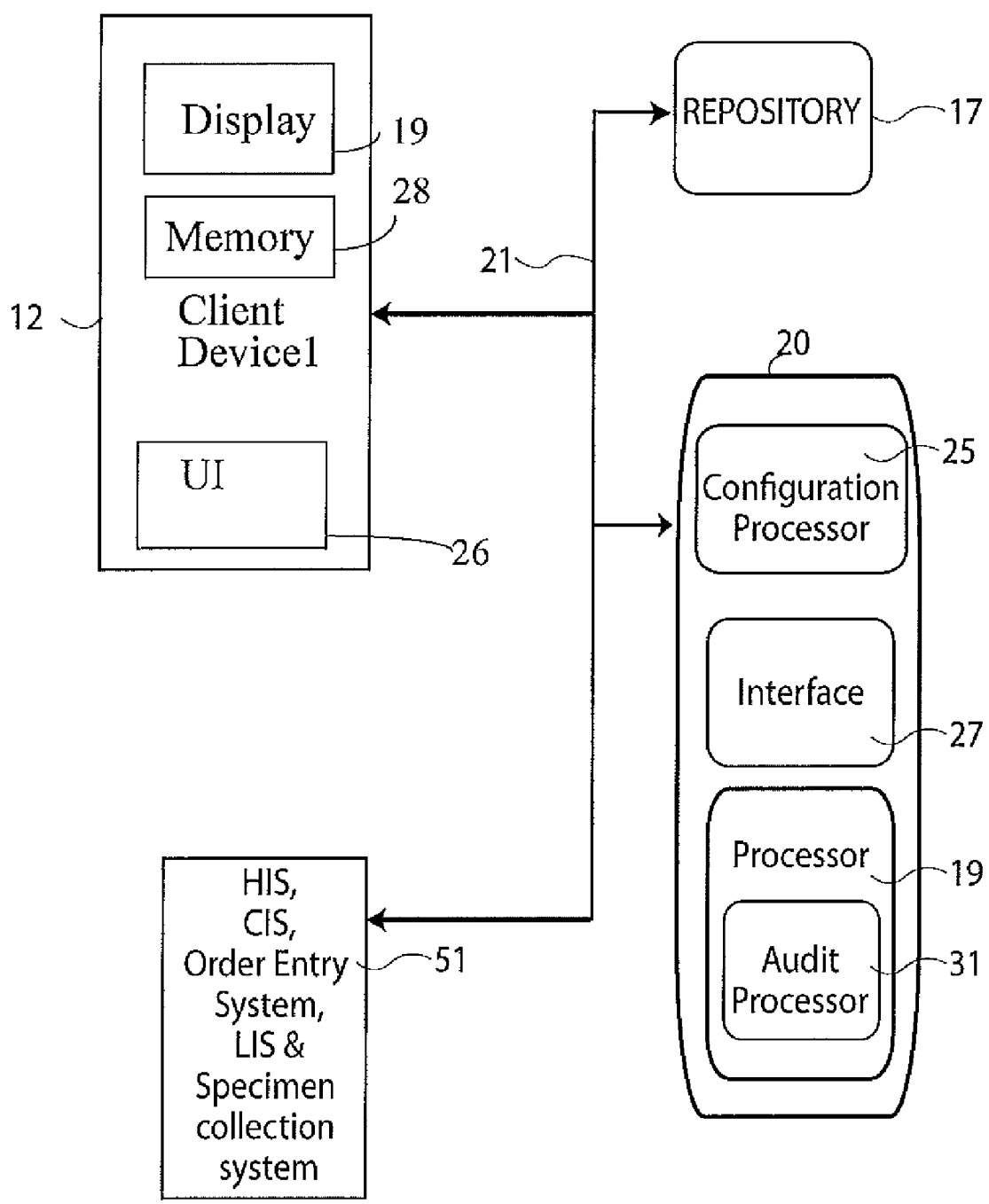
FIG. 1 shows an integrated point of care medication administration information system, according to invention principles.

FIG. 1 shows integrated point of care medication administration information system 10. System 10 includes client (processing) device 12 comprising a computer, workstation, notebook, PDA, phone or other device including a user interface 26, memory 28 and display 19. Device 12 bidirectionally inter-communicates via network 21 with point of care medication administration system 20 and at least one repository 17 as well as hospital systems 51. Hospital systems 51 include a hospital information system (HIS), laboratory information system (LIS), computerized order-entry system, pharmacy information system, specimen collection system and clinical information system (CIS). A point of care medication administration system 20 (including a Bar-code Point of Care system (BPOC) comprises a computer, or other processing device and includes interface 27, processor 19 and configuration processor 25. System 20 in one embodiment includes device 12. At least one repository 17 includes drug master files used by a pharmacy information system and information associating individual medications of multiple different medications with data identifying patient parameters and laboratory test results to be acquired and recorded prior to administration of an individual medication to a patient and identifying information sources for providing corresponding particular patient parameters and laboratory test results.

Point of care medication administration information system 20 includes interface 27 for communicating with at least one repository 17 and the information sources. Point of care medication administration system 20 in one embodiment is a mobile system for use at a patient bed side. Processor 19 uses information from at least one repository 17 and interface 27 in automatically acquiring for a particular patient data representing particular patient parameters and laboratory test results associated with a particular individual medication in response to user initiation of an order for the particular individual medication to be administered to the particular patient. Display device 19 presents at least one display image indicating acquired particular patient parameters and laboratory test results of the particular patient and identifying a particular patient parameter or laboratory test result needing to be acquired prior to administration of the particular individual medication to the particular patient.

System 10 identifies data elements for a specific medication. These data elements and their sources and associated acquisition communication data (addresses, location, format, communication protocols) are identified within pharmacy information system 51 master files. The data elements are acquired from the identified sources (e.g., other systems such as, a Laboratory information system, smart IV pumps, glucose meters, monitoring systems such as ECG monitors, and pulse oximeter monitors) at the point of medication administration by processor 19 in point of care system 20. The acquired data elements are automatically populated in specific data fields in memory in point of care system 20 enabling a clinician to evaluate patient status prior to medication administration. The data in the point of care system is stored at the occurrence level allowing data to later be retrieved for additional clinical evaluation. Thereby, for example, a nurse who needs to rely on results being readily accessible and correctly reported, benefits from having data automatically sent to a point of care system 20 application. Also, a clinician may make treatment therapy changes based upon documented results or vital signs that are advantageously automatically presented in a format identifying a trend over time and are associated with a specific dose and time of medication administration.

Figure 2:
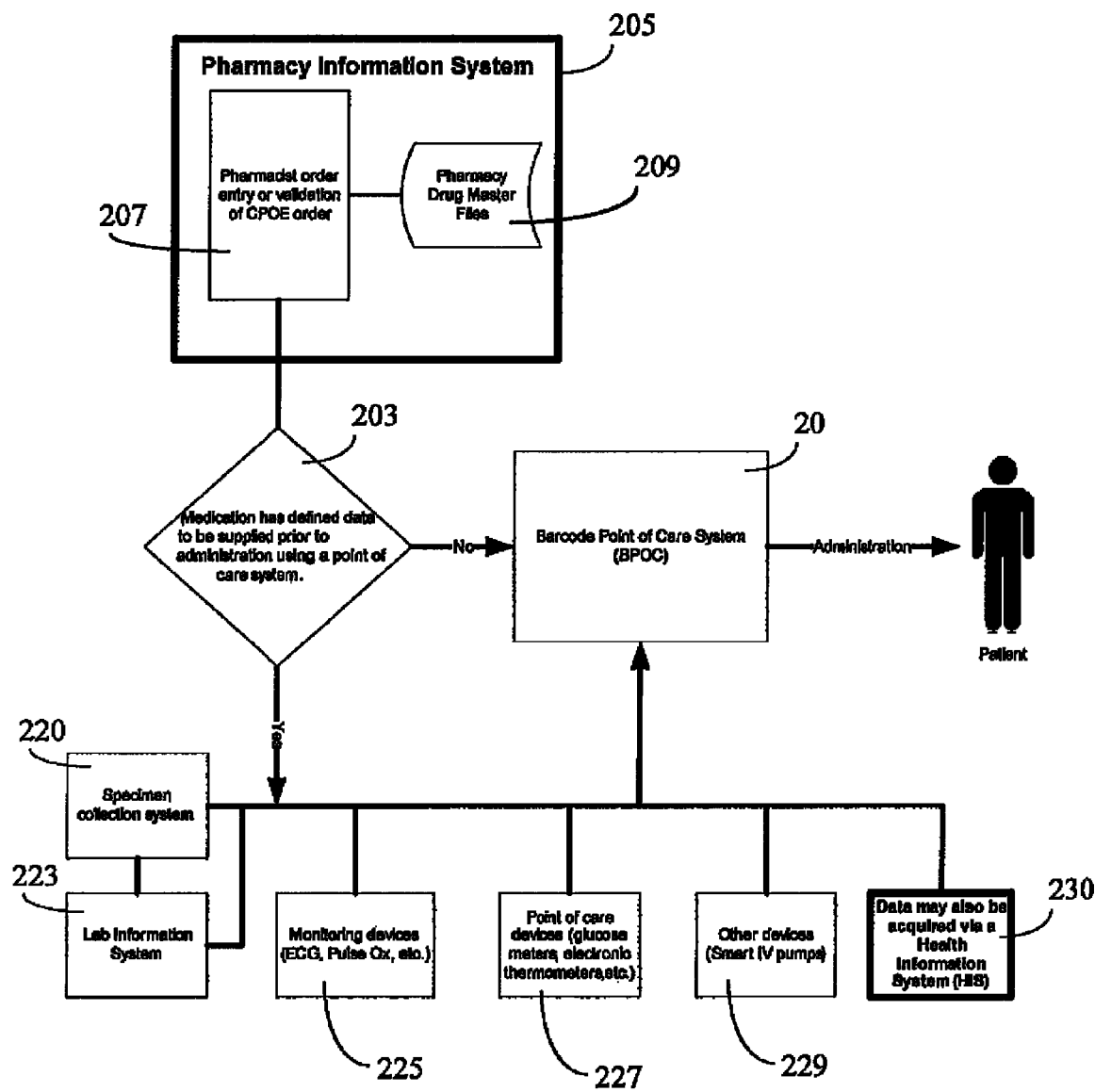
FIG. 2 shows an integrated point of care medication administration information system data flow, according to invention principles.

FIG. 2 shows an integrated point of care medication administration information system data flow. As medications are ordered via a computerized physician order entry (CPOE) system or directly entered in to a pharmacy information system, the system acquires specific data elements prior to administration using point of care system 20 (FIG. 1). Specifically in response to a pharmacist using pharmacy information system 205 for entering or validating an order 207 for medication to be administered to a patient via a computerized order entry (CPOE) system, point of care system 20 determines in step 203 whether the medication is associated with predetermined information to be provided to a clinician administering the medication prior to the administration. Point of care system 20 uses information in master files 209 in pharmacy information system 205, to identify required data elements and their data sources. Medication master files 209 identify individual medications that require a specific laboratory test result or vital sign data to be recorded prior to medication administration. Master files 209 identify specific data elements required (e.g., Pulse, heart rate, aPTT, INR) and identify the source of the data (e.g., INR located in Laboratory information system 223).

The required data elements are presented to a user upon administration of the medication on a display (e.g., display 19 FIG. 1). Master files 209 identify data sources and their associated communication data (addresses, location, format, communication protocols) used to acquire the data elements from the data sources. The acquired data is stored in appropriate corresponding data fields associated with the medication concerned in a repository (e.g., repository 17 FIG. 1). Point of care system 20 uses information in master files 209 in automatically interrogating data sources and acquiring for a particular patient, data representing particular patient parameters and laboratory test results associated with a particular individual medication. The data sources interrogated include specimen collection system 220, laboratory information system 223, patient monitoring devices 225 (ECG, blood oxygen saturation, blood pressure, for example), point of care devices 227 (glucose meters, electronic thermometers, for example), other devices (smart infusion pumps) 229 and HIS 230. Repository 17 (FIG. 1) used by point of care system 20 includes user determinable fields for storing displayable vital signs and laboratory test results. The data elements that are displayed or to be captured for a specific medication, are customizable by hospital, department or clinician. Further, in order to reduce the risk of recording data in an incorrect field, displayed data fields are limited to those for capturing required data elements of a medication concerned. User interface 26 provides selectable options in a display image enabling a clinician to edit, confirm or delete acquired data elements in point of care system 20. If system 20 is configured to inhibit editing, the information is "view only". If editing is allowed, the user is able to change the displayed data, and an audit record by audit processor 31 is maintained indicating changes to original data.

Configuration processor 25 (FIG. 1) enables a user to determine data required to be presented upon administration of the medication, the sources of the information and to indicate whether data required to be captured at the time of medication administration can be overridden if it is not available or if it is outside of predetermined ranges. Specifically, configuration processor 25 enables a user to enter configuration data determining patient parameters and laboratory test results to be acquired and recorded prior to administration of an individual medication. Processor 25 enables a user to determine acceptable value ranges of data required to be captured at the time of medication administration and to select a medication that allows a pharmacist to determine mandatory or optional data capture of particular data elements prior to, or after, time of medication administration.

At the time of medication administration by a clinician using point of care system 20, system 20 acquires the required data elements from the source locations and populates predefined fields in repository 17 (which in one embodiment is within system 20). System 20 also generates an alert message to notify a clinician when required data is not available. Configuration processor 25 provides user selectable set-up options in a display image enabling a clinician to override an alert and continue to manually document information, or terminate administration. Overrides are documented by system 20 for audit tracking. At the completion of medication administration and charting with point of care system 20, laboratory test results and vital sign data is stored together with information documenting medication administration. The documented data is available for view within a charted occurrence (event) history for each administration. Configuration processor 25 enables a user to enter data determining time, date and frequency parameters for individual data elements to be captured or displayed at time of medication administration. These parameters allow system 20 to present relevant data to a clinician prior to medication administration. System 20 alerts a clinician if a captured or received data element value falls outside the predetermined parameters.

In operation, a warfarin dose is to be administered today at 5 PM, for example, however, the last reported INR in the laboratory system was beyond the set 24-hour limit indicated in the pharmacy master files. INR (International normalized ratio) is used for reporting the results of blood coagulation (clotting) tests. System 10 alerts a user of point of care system 20 that INR data is acquired at a time outside a reporting time limit and is outside hospital policy for appropriate evaluation of the INR. In a further example of operation, a heparin bolus is scanned using a bar code scanner for administration using point of care system 20. However, data received from a smart IV pump and the last recorded aPTT value indicates that only two hours have passed since the last heparin rate change. The system alerts the clinician that another aPTT needs to be reported prior to making a dose change. In another example, a Gentamicin 80 mg IV dose is entered together with an order for a daily gentamicin level using a CPOE system. Two doses are administered and the gentamicin level is captured with each administration (in this example, the gentamicin plasma level data is acquired from a laboratory information system). During system set-up using configuration processor 25, a parameter is set to alert a clinician whether information is recorded prior to at least four doses being administered to indicate that a steady state plasma concentration may not have been achieved and that peak levels prior to the fourth dose may not reflect an adequate response to the medication. An alert message generated by system 10 informs a clinician that reported peak levels may not accurately reflect a desired response to the medication prior to the fourth dose being administered.

Some medications may require that data such as laboratory test results or vital signs are recorded when the medication is used for a specific indication or under certain conditions. Configuration processor 25 enables configuration of pharmacy system drug master files to require patient laboratory test results, vital sign data and other data in response to occurrence of a specific condition such as a particular patient parameter, or test result value or combination of values or other indication. In one embodiment of system 10, a pharmacist initiates a process for prompting a user to acquire data associated with administration of a particular medication using point of care system 20 at the time of order entry using a pharmacy system. In an example of operation. Acetaminophen is ordered for a patient as 650 mg PO PRN temperature greater than 101° F. Acetaminophen can also be used to treat pain, but in this case the fever indication requires the documentation of temperature at the time of administration. A workflow directed by a workflow processor (not shown to preserve drawing clarity) within processor 19 prompts a pharmacist to select an option within a display image provided by a pharmacy information system at the time of order entry or validation to initiate acquisition of temperature information. The temperature information is acquired from an electronic temperature device employed by point of care system 22 at the time of medication administration or requires a nurse to acquire the temperature if the data cannot be automatically acquired.

System 10 presents a display image on unit 19 that prompts a user to indicate patient medical data acquired at the point of medication administration has been reviewed or that auto populated data has been reviewed for clinical documentation and audit purposes. Specifically, system 10 records a user identifier such as user ID or name identifying a reviewer of the patient medical data. User interface functions on display 19 are facilitated by a cursor hover function whereby in response to a user positioning a cursor over a specific patient medical result or laboratory test data value, display 19 presents an image indicating a last corresponding previous result or laboratory test data value together with an associated date and time it was recorded.

A specimen collection system in unit 51 (FIG. 1) is integrated within system 10 to qualify data that is presented to a user in response to a Patient Identification Check, for example. In operation, for example, a heparin continuous infusion is initiated and an aPTT is drawn an hour after the start of the infusion. A specimen collection system is used to identify the patient and date and time of the sample. System 10 is configured using configuration processor 25 to generate an alert message for presentation on display 19 alerting a user of point of care system 20 that aPTT (activated partial thromboplastin time) data acquired less than 4 hours after start of an IV heparin infusion may be super-therapeutic and does not represent an accurate response to heparin. Further, display 19 presents an image using a visual attribute to identify a medication that requires results to be supplied by another system, e.g. a Laboratory information system (a "pending" result) or a result that has not been received. A visual attribute comprises a different color, a unique icon, shading or highlighting, for example and the display image comprises a worklist for point of care system 20 notifying a healthcare worker that a required result is not available. In addition, a message is automatically sent to an appropriate system notifying a clinician (e.g. a laboratory technician), via a message or prioritized work list notice, indicating to a user of point of care system 20 that a medication is to be administered within a specified time frame and associated data needs to be acquired.

In operation, a warfarin order, for example, requires an INR to be checked by a nurse prior to medication administration but a laboratory has not yet reported a daily INR result and a last reported INR result is from a previous day (outside of system set parameters for an appropriate INR evaluation). System 10 communicates data indicating an order to administer warfarin to a worklist of a user of point of care system 20 indicating that the warfarin needs to be administered. The warfarin order item on the worklist is identified by a visual attribute such as by being highlighted in a different color or with a unique icon, indicating that the INR data needed has not been supplied yet by the laboratory system for that day. System 10 tracks specific doses of warfarin and the corresponding INR assists a physician in tailoring dose changes. Point of care system 20 automatically sends a notice to a worklist of a user of the laboratory information system alerting a laboratory worker that a patient requires the INR result to be reported as soon as possible, because the medication is on an active worklist of a user of point of care system 20. Point of care system 20 is integrated with a specimen collection system enabling system 20 to present a user with additional status information via display 19 such as an indication a specimen has been or has not yet been collected. An additional function performed by system 20 detects and notifies a clinician via a worklist on a CPOE system, of a failure to order a laboratory test required for administration of a specific medication.

System 20 stores data in repository 17 and processes the data for generating reports for tracking and indicating a trend in laboratory test results and vital sign data and other data. This information is stored in association with occurrences and administration event indication data so that a particular dose of medication is associated with a specific result and vital sign. System 10 automatically acquires data from various electronic sources and presents the acquired data to a clinician at the time of administration via display 19. This reduces replication of effort and need to search for data in other systems. Data qualifiers ensure that data presented is appropriate. This increases patient safety and positive outcomes. System 10 is used by nurses and other clinicians responsible for medication administration using a point of care system. A physician may be remote from a user of data that is captured using the system.

FIG. 3 shows a flowchart of a process used by integrated point of care medication administration information system 10. In step 302 following the start at step 301, system 10 (FIG. 1) stores in at least one repository 17 information associating individual medications of multiple different medications with data identifying patient parameters and laboratory test results to be acquired and recorded prior to administration of an individual medication to a patient and identifying data sources for providing corresponding particular patient parameters and laboratory test results. At least one repository 17 of information associates a time and date with an individual patient parameter or laboratory test result indicating when the individual patient parameter or laboratory test result needs to be acquired and recorded prior to administration of the individual medication. The information associates a frequency with which the individual patient parameter or laboratory test result needs to be acquired and recorded prior to administration of the individual medication. The information also associates a condition with an individual medication indicating a patient parameter or laboratory test result is acquired and recorded only if the individual medication is used for treating a particular medical condition.

In step 307 interface 27 communicates with at least one repository 17 and the sources and processor 19 uses the information in automatically acquiring for a particular patient data representing particular patient parameters and laboratory test results associated with a particular individual medication from the sources in response to user initiation of an order for the particular individual medication to be administered to the particular patient. The sources that provide corresponding particular patient parameters and laboratory test results comprise one or more of, (a) patient monitoring devices, (b) a laboratory information system, (c) a specimen collection information system, (d) a healthcare information system, (e) a patient medical record, (f) a pharmacy information system and (g) infusion pumps. Processor 19 automatically acquires the data representing particular patient parameters and laboratory test results in response to user initiation of an order for the particular individual medication via a computerized order entry system. Also, processor 19 initiates auto-population of medical record data fields, for use by point of care medication administration system 20, with the automatically acquired particular patient parameters and laboratory test results in response to user initiation of an order for the particular individual medication to be administered to the particular patient.

In step 311, system 10 acquires data indicating a date and time of acquisition of a specimen used for a laboratory test from a specimen collection information system and acquires data indicating status of a laboratory test from a laboratory information system. In step 314 display 19 presents at least one display image indicating acquired particular patient parameters and laboratory test results of the particular patient and identifying a particular patient parameter or laboratory test result needing to be acquired prior to administration of the particular individual medication to the particular patient. At least one repository 17 of information associates specimen acquisition usage conditions with an individual medication enabling generation of an alert message for communication to a user indicating that a laboratory test result may be invalid because the date and time of acquisition exceeds a limit set by the acquisition usage conditions. The at least one display image presents an alert message identifying a particular patient parameter or laboratory test result needing to be acquired and that was not automatically acquired and presents display elements enabling a user to override the alert message. An audit processor 31 within processor 19 automatically generates a record of an override. The at least one display image also presents display elements indicating status of the laboratory test. The process of FIG. 3 terminates at step 321.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

Processor 19 includes a workflow processor to determine tasks to add to a task list, remove from a task list or modify tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

The system and processes of FIGS. 1-3 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system enables a user to configure specific parameters, for individual medications, to ensure that information presented to a clinician has been acquired and documented at time of medication administration, for example, enabling prospective medication management decisions and tracking and identifying a trend in responses to medications over time. Further, the processes and applications may, in alternative embodiments, be located on one or more (e.g., distributed) processing devices on a network linking the units of FIG. 1. Any of the functions and steps provided in FIGS. 1-3 may be implemented in hardware, software or a combination of both.

What is claimed is:

1. An integrated point of care medication administration system, comprising:

at least one repository of information associating individual medications of a plurality of different medications with data identifying patient parameters and laboratory test results to be acquired and recorded prior to administration of an individual medication to a patient and identifying data sources for providing corresponding particular patient parameters and laboratory test results, said at least one repository of information associating specimen acquisition usage conditions with an individual medication enabling generation of an alert to a user that a laboratory test result may be invalid because said date and time of acquisition exceeds a limit set by said acquisition usage conditions;

a specimen collection information system providing data indicating a date and time of acquisition of a specimen used for a laboratory test; and a point of care medication administration system including, an interface for communicating with said at least one repository and said sources, a processor for using said information and said interface in automatically acquiring for a particular patient data representing particular patient parameters and laboratory test results associated with a particular individual medication in response to user initiation of an order for said particular individual medication to be administered to said particular patient and a display device for presenting at least one display image indicating acquired particular patient parameters and laboratory test results of said particular patient and identifying a particular patient parameter or laboratory test result needing to be acquired prior to administration of said particular individual medication to said particular patient.

2. A system according to claim 1, wherein
said point of care medication administration system is a mobile system for use at a patient bed side and
said, at least one repository of information includes drug master files used by a pharmacy information system.

3. A system according to claim 2, including
a configuration processor enabling a user to enter configuration data determining patient parameters and laboratory test results to be acquired and recorded prior to administration of an individual medication.

4. A system according to claim 1, wherein
said processor automatically acquires said data representing particular patient parameters and laboratory test results in response to user initiation of an order for said particular individual medication via a computerized order entry system.

5. A system according to claim 1, wherein
said at least one display image presents an alert message identifying a particular patient parameter or laboratory test result needing to be acquired and was not automatically acquired.

6. A system according to claim 5, wherein
said at least one display image presents display elements enabling a user to override said alert message and including
an audit processor for automatically generating a record of an override.

7. A system according to claim 1, wherein
said sources for providing corresponding particular patient parameters and laboratory test results comprise at least two of, (a) patient monitoring devices, (b) a laboratory information system and (c) a specimen collection information system.

8. A system according to claim 7, wherein
said sources for providing corresponding particular patient parameters and laboratory test results comprise at least two of, (i) a healthcare information system, (ii) a patient medical record, (iii) a pharmacy information system and (iv) infusion pumps.

9. A system according to claim 1, wherein
said point of care medication administration system comprises a bar-code point of care system.

10. A system according to claim 1, wherein
said processor initiates auto-population of medical record data fields, for use by the point of care medication administration system, with the automatically acquired particular patient parameters and laboratory test results in response to user initiation of an order for said particular individual medication to be administered to said particular patient.

11. A system according to claim 1, wherein
said at least one repository of information associates a time and date with an individual patient parameter or laboratory test result indicating when said individual patient parameter or laboratory test result needs to be acquired and recorded prior to administration of said individual medication.

12. A system according to claim 11, wherein
said at least one repository of information associates a frequency with which said individual patient parameter or laboratory test result needs to be acquired and recorded prior to administration of said individual medication.

13. A system according to claim 1, wherein
said at least one repository of information associates a condition with an individual medication indicating a patient parameter or laboratory test result is acquired and recorded only if the individual medication is used for treating a particular medical condition.

14. A system according to claim 1, including
a laboratory information system providing data indicating status of a laboratory test and
said at least one display image presents display elements indicating status of the laboratory test.

15. A method for documenting medication administration, comprising the activities:
storing in at least one computer repository of information associating individual medications of a plurality of different medications with data identifying patient parameters and laboratory test results to be acquired and recorded prior to administration of an individual medication to a patient and identifying data sources for providing corresponding particular patient parameters and laboratory test results, said at least one repository of information associating specimen acquisition usage conditions with an individual medication enabling generation of an alert to a user that a laboratory test result may be invalid because said date and time of acquisition exceeds a limit set by said acquisition usage conditions;
providing data indicating a date and time of acquisition of a specimen used for a laboratory test;
communicating with said at least one repository and said sources,
using said information in automatically acquiring for a particular patient data representing particular patient parameters and laboratory test results associated with a particular individual medication in response to user initiation of an order for said particular individual medication to be administered to said particular patient; and
presenting, using a display device, at least one display image indicating acquired particular patient parameters and laboratory test results of said particular patient and identifying a particular patient parameter or laboratory test result needing to be acquired prior to administration of said particular individual medication to said particular patient.

* * * * *